(12) United States Patent
Cancedda et al.

(10) Patent No.: US 7,109,032 B2
(45) Date of Patent: Sep. 19, 2006

(54) SERUM-FREE MEDIUM FOR MESENCHYMAL STEM CELLS

(75) Inventors: Ranieri Cancedda, Genoa (IT); Beatrice Dozin, Rapallo (IT)

(73) Assignees: Consorzio per la Gestione del Centro di Biotecnologie Avanzate, Genoa (IT); Istituto Nazionale per la Ricerca Sul Cancro, Genoa (IT)

( * ) Notice: Subject to any disclaimer, the term of this patent is extended or adjusted under 35 U.S.C. 154(b) by 339 days.

(21) Appl. No.: 10/614,191

(22) Filed: Jul. 8, 2003

(65) Prior Publication Data

US 2005/0090002 A1  Apr. 28, 2005

Related U.S. Application Data

(62) Division of application No. 09/831,161, filed as application No. PCT/EP99/08482 on Nov. 8, 1999, now Pat. No. 6,617,159.

(60) Provisional application No. 60/107,646, filed on Nov. 9, 1998.

(51) Int. Cl.
 *C12N 5/00* (2006.01)
 *C12N 5/02* (2006.01)
(52) U.S. Cl. ............... 435/404; 435/325; 435/405
(58) Field of Classification Search ............... None
 See application file for complete search history.

(56) References Cited

U.S. PATENT DOCUMENTS 5,405,772 A  4/1995  Ponting 5,962,325 A  10/1999  Naughton et al.

FOREIGN PATENT DOCUMENTS

| WO | WO96/39487 | 12/1996 |
|---|---|---|
| WO | WO96/40866 | 12/1996 |
| WO | WO97/33978 | 9/1997 |
| WO | WO98/04681 | 2/1998 |

OTHER PUBLICATIONS

Quarto R et al.: "Proliferation and differentiation of chondrocytes in defined culture medium: effects of systemic factors" BONE, vol. 17, No. 6, Dec. 1995, p. 558.
Pain B et al.: "Long-term in vitro culture and characterisation of avian embryonic stem cells with multiple morphogenetic potentialities" Development, GB, Colchester, Essex,vol. 122, Aug. 1996, pp. 2239-2248.

*Primary Examiner*—David M. Naff
*Assistant Examiner*—Deborah K. Ware
(74) *Attorney, Agent, or Firm*—Nixon & Vanderhye P P.C.

(57) ABSTRACT

Serum-free media for growth and proliferation of chondrocytes and mesenchymal stem cells in culture are provided. A serum-free medium for growth of chondrocytes includes a serum-free composition comprising FGF-2, linoleic acid, ascorbic acid, B-mercaptoethanol, transferrin and dexamethasone. Further, the composition comprises EGF, PDG-Fbb, insulin and albumin. A method for growing chondrocytes in a serum free medium comprising the compostion is also provided. Also provided for mesenchymal stem cell growth, is a serum-free medium which includes a composition comprising FGF-2, LIF, SCF, pantotenate, biotin and selenium and method, therefore.

8 Claims, 1 Drawing Sheet

SERUM-FREE MEDIUM FOR MESENCHYMAL STEM CELLS

The present application is divisional of application Ser. No. 09/831,161, filed Jun. 11, 2001 now U.S. Pat. No. 6,617,159 which is a 371 U.S. National Phase of PCT/EP99/08482, filed 8 Nov. 1999, which claims benefit of U.S. Provisional application Ser. No. 60/107,646, filed 9 Nov. 1998, the entire contents of each of which is incorporated herein by reference.

BACKGROUND OF THE INVENTION

Bone and cartilage transplantation is an absolute need in reconstruction of bone and cartilage segments in plastic surgery, traumatic surgery or after the removal of neoplastic lesions, etc. Typically, material of human (autologous, from donors or from cadavers) or animal origin has been used for this purpose. Given the increased demand from clinicians for transplant tissues, the increased need for microbial safety in tissue transplantation, the advances in cell biology, cell differentiation and tissue engineering, the concept of rebuilding tissues from autologous or allogeneic cells expanded in vitro has become a growing field in the world of biomedical sciences. Cellular sources for skeletal repair include chondrocytes and cells committed to the chondrocyte lineage, and mesenchymal stem cells, the former specific for cartilage, the latter multipotential and therefore having the potential to be used to replace bone, cartilage and other tissues.

Mesenchymal stem cells (MSCs) are found in bone marrow as well as in blood, dermis and periosteum. Although these cells are normally present at very low frequencies in bone marrow these cells can be isolated purified and culturally expanded, for example, as described in U.S. Pat. No. 5,486,359.

Typically, the in vitro expansion of chondrocytes and MSCs takes place in culture medium supplemented with bovine serum or optimally with autologous serum from the patient. However, the presence of animal or autologous serum in chondrocyte and MSC cultures has certain disadvantages and limitations in view of the potential therapeutical applications of these cultures.

For example, serum is not the physiological fluid most cells closely contact in tissue in vivo. This is particularly true for chondrocytes that, in vivo, are embedded in their avascularized matrix and rely for their own growth and differentiation on various growth factors and cytokines acting in an autocrine/panacrine manner rather than diffusing from the distant bloodstream. Further, there is often high variability between animal serum batches. Extensive serum screening required to select the batch most representative of the in vivo inductive effects can be time-consuming and expensive The preparation of autologous serum from patients is also time consuming and supplies are limited. Animal serum can further potentially carry unknown pathogens with consequent risk of contamination for the patient.

Thus, serum substitutes for culturing cells for potential in vivo therapeutic applications is desirable.

SUMMARY OF THE INVENTION

The present invention provides a serum substitute for culturing cells in vitro using well defined factors able to support cell viability, proliferation and differentiation as effectively as serum containing medium. In a preferred embodiment, the cells are articular chondrocytes or mesenchymal stem cells.

In one aspect, the invention comprises a composition for the expansion of chondrocytes, comprising a minimum essential medium, a growth factor, albumin, a steroid, an antioxidant, an iron source, a fatty acid and/or a lipid source, and insulin. In a particularly preferred embodiment, the serum free growth medium for chondrocytes comprises Fibroblast Growth Factor 2 (FGF-2) as a growth factor, linoleic acid as the lipid/fatty acid source, ascorbic acid and β-mercaptoethanol as antioxidants, holo- and apo-transferrin as the iron source, and dexamethasone as a steroid. Optional ingredients can include cholesterol, trace metals such as selenium, and vitamins such as biotin and sodium pantotenate.

In another aspect, the invention comprises a composition for the maintenance of mesenchymal stem cells, comprising a growth factor, albumin, a steroid, an antioxidant, an iron source, a fatty acid and/or a lipid source, one or more vitamins, one or more trace metals, and Insulin Growth Factor I (IGF-1), in combination with a minimum essential medium. In a particularly preferred embodiment, the serum free growth medium for mesenchymal stem cells comprises FGF-2, Leukemia Inhibitory Factor (LIF) and Stem Cell Factor(SCF) as growth factors, sodium pantotenate and biotin as vitamins, and selenium as a trace metal.

DETAILED DESCRIPTION OF THE INVENTION

Figure 1:
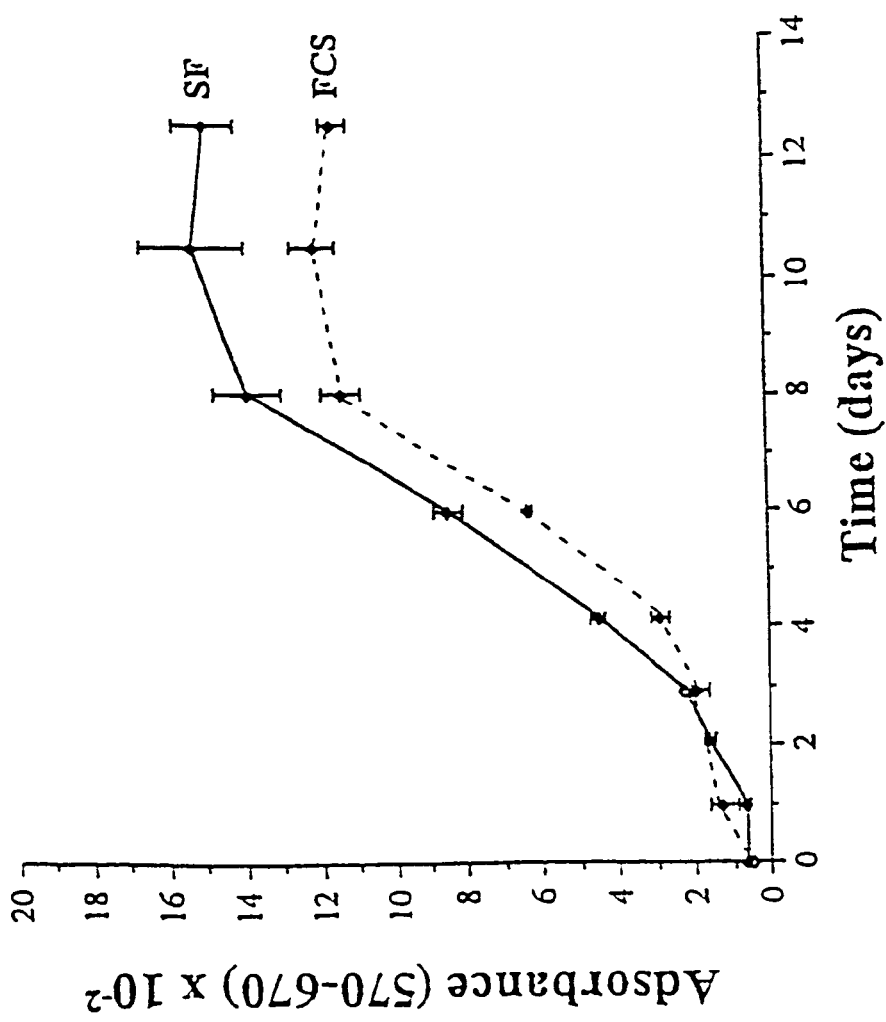
FIG. 1 shows the comparison of articular chondrocyte growth kinetics in medium containing FCS and the serum free medium of the present invention.

The present invention provides serum free compositions suitable for chondrocyte and mesenchymal stem cell growth and proliferation. The compositions may include in a base minimum essential medium, such as Coon's modified Ham's F-12 medium, the following components as a substitute for serum:

i) one or more growth factors or proteins which cause resting cells to undergo cell division and/or differentiation, such as insulin, FGF-2, Platelet-Derived Growth Factor bb(PDGFbb), Epiderman Growth Factor(EGF), LIF and SCF and IGF-1;

ii) one or more steroids such as dexamethasone;

iii) one or more sources of lipids and fatty acids, necessary for cell membrane biosynthesis, such as cholesterol and linoleic acid; and iv) an iron source such as transferrin.

FGF-2, PDGFbb and EGF are potent mitogens for cells of mesenchymal origin. Dexamethasone is known to keep cells in a cycling phase in vitro.

The serum free medium of the present invention may further comprise:

i) albumin (preferably of mammalian species) which functions as an aspecific carrier;

ii) one or more antioxidants such as β-mercaptoethanol;

iii) a supplement for coenzyme transport in carboxyl group transfer reactions, such as biotin;

iv) trace elements as a supplemental source of metal necessary for electron transport and many metalloenzymes and proteins, such as selenium;

v) vitamins, such as biotin and pantotenate; and vi) ascorbic acid, to facilitate organization of the extracellular matrix.

Insulin and dexamethasone are added at the average concentrations usually reported in the literature.

IGF-I, LIF and SCF are present at concentrations in the range from about 5 to about 10 ng/ml; preferably at a concentration of 5 ng/ml. All the other components are included in a range of concentration typically used in cell culture studies.

In a preferred embodiment of the composition suitable for the growth and proliferation of the chondrocytes, the defined components comprise EGF, PDGFbb and FGF-2, ascorbic acid, linoleic acid, human serum albumin (HSA), β-mercaptoethanol, dexamethasone, insulin, human holo- and apo-transferrin. In this embodiment, FGF-2, PDGFbb and EGF are present at concentrations in the range of from about 1 to about 10 ng/ml. In a preferred embodiment, FGF-2, PDGFbb and EGF are present at concentrations of from 1 to 2 ng/ml.

In a preferred embodiment of the composition suitable for the growth and proliferation of the mesenchymal stem cells, the defined components comprise EGF, PDGFbb and FGF-2, LIF, SCF, IGF-I, ascorbic acid, cholesterol, HSA, β-mercaptoethanol, dexamethasone, human holo- and apo-transferrin, selenium, biotin, sodium pantotenate. FGF-2, PDGFbb and EGF are present at concentrations in the range of from about 5 ng/ml to about 10 ng/ml of each factor. The preferred concentrations of FGF-2, PDGFbb and EGF are 10 ng/ml. FGF-2 alone was found to be the most active factor for maintenance of osteochondrogenic potential in MSCs.

EXAMPLE 1

Articular cartilage was harvested from the knee joint of young adult human donors. The samples were first cleaned of any adherent muscular, connective or subchondral bone tissues, minced into 1–3 mm fragments and rinsed in PBS. Single chondrocytes were then released by repeated enzymatic digestions at 37° C. with 0.25% trypsin, 400 U/ml collagenase I, 1000 U/ml collagenase II and 1 mg/ml hyaluronidase. Trypsin was then blocked and removed by rapid and extensive washes in PBS containing soybean trypsin inhibitor. Cells were plated in anchorage-dependent conditions in Coon's modified Ham's F-12 medium supplemented either with 10% fetal calf serum (FCS, control culture) or the following defined components: EGF, PDGFbb and FGF-2, ascorbic acid, linoleic acid, human serum albumin (HSA), β-mercaptoethanol, dexamethasone, insulin, human holo- and apo-transferrin. Table 1 below shows the preferred amounts of each component. To favor adhesion of the cells in serum free conditions, the dishes were pre-coated with 2% gelatin.

Insulin may not be substituted with IGF-1 in the medium for chondrocytes. Insulin was preferably at a concentration of 5 μg/ml. Selenium, biotin, sodium pantotenate and cholesterol can be routinely included but are optional.

TABLE 1

Medium Supplement for Serum Free Expansion of Human Chondrocytes

| INGREDIENT | CONCENTRATION |
|---|---|
| (Basal medium: Coon's modified Ham's F12) | |
| FGF-2 | 1–10 ng/ml |
| PDGFbb | 1–10 ng/ml |
| EGF | 1–10 ng/ml |
| Insulin | 5 μg/ml |

TABLE 1-continued

Medium Supplement for Serum Free Expansion of Human Chondrocytes

| INGREDIENT | CONCENTRATION |
|---|---|
| Dexamethasone | $10^{-8}$ M |
| Ascorbic Acid | 50 μg/ml |
| Transferrin | 20–50 μg/ml |
| HSA | 1% |
| Linoleic Acid | 6 μM |
| β-mercaptoethanol | $5 \times 10^{-5}$ M |

EXAMPLE 2

Bone marrow sample harvested from the iliac crest of the patient was washed twice with PBS. The nucleated cells were counted using methyl violet and plated at $5 \times 10^6$ cells as unfractionated marrow per 10 cm tissue culture dish. For selection and expansion, the cells were maintained in Coon's modified Ham's F12 (F12) supplemented either with 10% FCS and 1 ng/ml FGF-2 (control culture) or the following defined components: EGF, PDGFbb, FGF-2, LIF, SCF, IGF-I, ascorbic acid, cholesterol, HSA, β-mercaptoethanol, dexamethasone, human holo- and apo-transferrin, selenium, biotin and sodium pantotenate. Table 2 below shows the preferred amounts of each component. To favor adhesion of the MSCs, the cells were first plated for 48 hours in F12 medium supplemented with 10% human serum and 1 ng/ml FGF-2. Thereafter, the medium was removed and the cells were extensively washed with PBS, and left for an additional 24–48 hours in F12 medium without any supplement. The defined mixture of factors was then added to promote cell proliferation.

FGF-2 alone was the most active factor for maintenance of osteochondrogenic potential in mesenchymal stem cells. Selenium, biotin and sodium pantotenate were preferably included for cell viability. LIF and SCF were seen to improve the extent of cell proliferation, in particular in combination with IGF-1.

TABLE 2

Medium Supplement for Serum Free Expansion of MSCs

| INGREDIENT | CONCENTRATION |
|---|---|
| (Basal medium: Coon's modified Ham's F12) | |
| Human serum albumin | 1–2% |
| Transferrin (apo/holo) | 20–50 μg/ml |
| Ascorbic Acid | 50 μg/ml |
| β-mercaptoethanol | $5 \times 10^{-5}$ M |
| Cholesterol | 30 μg/ml |
| Selenium | 30 nM |
| Biotin | 33 μm |
| Na pantotenate | 17 μM |
| EGF/PDGF/FGF-2 | 1–10 ng/ml |
| Dexamethasone | $10^{-8}$ M |
| IGF-I | 5 ng/ml |
| LIF | 5 ng/ml |
| SCF | 5 ng/ml |

Studies have shown that PDGFbb by itself increases the osteogenic potential of MSCs when included in the phase of proliferation. This effect was found to be amplified by combining PDGFbb with FGF-2.

EXAMPLE 3

Growth Kinetics of Chondrocytes

At day 0, $5 \times 10^3$ first passage cells were plated in each well of a 24-well plate in the presence of FCS. Upon adhesion, the FCS was removed, and the cells were extensively washed with PBS and left for 2–3 days in F12 without supplement to exhaust residual traces of serum. Proliferation was then reinduced by adding either 10% FCS or the mixture of defined components established for chondrocytes. Cell number was evaluated at different days via Thiazolyl blue (MTT) staining. Briefly, culture medium was removed and replaced with 0.5 ml of medium without supplement; then 25 µl MTT (Sigma, St. Louis, Mo.) stock solution (5 mg/ml) was added to each culture being assayed. After a 3 hour incubation the medium was removed and the converted dye solubilized with absolute ethanol. Absorbance of converted dye was measured at a wavelength of 570 nm with background subtraction at 670 nm.

The data obtained (see FIG. 1) clearly show that the defined medium induces the chondrocytes to proliferate to a rate and extent comparable to those obtained in the presence of FCS.

EXAMPLE 4

The differentiation potential of the chondrocytes expanded in serum free conditions was tested both in vitro and in vivo. For in vitro assay, the expanded cells were transferred in anchorage-independent conditions and maintained as a pellet culture for 2–4 weeks in the serum free medium previously shown by Johnstone et al. (Johnstone, B., Hering, T. M., Caplan, A. I., Goldberg, V. M. and Yoo, J. U. Exp. Cell Res. 238, 265–272, 1998) to induce chondrogenesis of serum expanded MSCs.

For in vivo assay, the expanded cells were implanted for 2 to 8 weeks in athymic mice either as a dense cell suspension or after embeddment in fibrin gel (Tissucol). At the term of the assays, the samples were fixed in formalin, embedded in paraffin and sectioned. Serial sections were processed for histological (toluidine blue and alcian blue) analysis and immunohistochemistry with collagen-specific antibodies.

Results indicated that, at variance with chondrocytes expanded in the presence of FCS, the chondrocytes expanded in serum free conditions-directly reformed a cartilaginous structure both in vitro and in vivo, which stained metachromatic for toluidine blue, positive for alcian blue and type II collagen, and mostly negative for type I collagen. In contrast, in the case of the expansion in FCS, a total absence of full chondrogensis was observed both in vitro and in vivo; at most, a faint metachromatic staining was detected in some pellet cultures, but they always lacked well defined lacunae and well organized extracellular matrix.

These data illustrate a major advantage of the serum free system that allows chondrogenesis without the requirement of additional culturing in the presence of TGF-β 1 or other factors (Johnstone's inducing conditions). This may be due to the fact that chondrocytes, in nature, are not in contact with serum which may contain elements that inhibit chondrogenesis.

EXAMPLE 5

The osteogenic potential of MSCs after expansion under serum free defined conditions was tested in vivo by implantation of the expanded cells in athymic mice after adsorption on collagraft.

Several combinations of conditions were tested for bone formation in vivo. For all factor combinations, the medium contained Coon's modified Ham's F-12, dexamethasone, FGF-2, PDGFbb, EGF, transferrin, cholesterol, human serum albumin, biotin, selenium, Na pantotenate and ascorbic acid (concentrations as in Table 2). The combinations tested were 1) insulin; 2) IGF-1; 3) insulin and LIF; 4) insulin and SCF; 5) insulin, LIF and SCF; 6) IGF-1 and LIF; 7) IGF-1 and SCF; and 8) IGF-1, LIF and SCF.

After 8 weeks of implantation, the samples were decalcified, included and processed for histology as above. The sections were stained with hematoxylin-eosin. All the conditions of expansion allowed the MSCs to reform bone tissue in vivo; however, the amount of bone formed varied from condition to condition. The combination of IGF-1, LIF and SCF provided an optimal expansion environment among the combinations tested.

The invention claimed is:

1. A method for culturing mesenchymal stem cells, which comprises growing said cells in a serum-free composition comprising FGF-2, LIF, SCF, pantothenate biotin and selenium.

2. The method according to claim 1, wherein the serum-free composition further comprises EGF, PDGFbb, IGF-1, ascorbic acid, cholesterol, albumin, β-mercaptoethanol, dexamethasone and transferrin.

3. The method according to claim 1, wherein the serum-free composition further comprises a minimum essential medium.

4. The method according to claim 2, wherein the serum-free composition further comprises a minimum essential medium.

5. A serum-free culture medium for mesenchymal stem cells comprising FGF-2, LIF, SCF, pantothenate, biotin and selenium.

6. The serum-free culture medium according to claim 5, further comprising EGF, PDGFbb, IGF-1, ascorbic acid, cholesterol, albumin, β-mercaptoethanol, dexamethasone and transferrin.

7. The serum-free culture medium according to claim 5 further comprising a minimum essential medium.

8. The serum-free culture medium according to claim 6 further comprising a minimum essential medium.

* * * * *